United States Patent [19]
Bertin et al.

[11] Patent Number: 5,853,415
[45] Date of Patent: *Dec. 29, 1998

[54] FEMORAL MILLING INSTRUMENTATION FOR USE IN TOTAL KNEE ARTHROPLASTY WITH OPTIONAL CUTTING GUIDE ATTACHMENT

[75] Inventors: Kim C. Bertin, Bountiful, Utah; Dennis W. Burke, Milton, Mass.; Gregory C. Stalcup, Columbia City, Ind.; Rodney Bays, Pierceton, Ind.; Richard D. Vanlaningham, Leesburg, Ind.; Terry L. Dietz, Columbia City, Ind.; Daniel O'Connor, East Taunton, Mass.

[73] Assignee: Zimmer, Inc., Warsaw, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 432,481

[22] Filed: May 1, 1995

Related U.S. Application Data

[60] Division of Ser. No. 169,459, Dec. 17, 1993, Pat. No. 5,474,559, which is a continuation-in-part of Ser. No. 087,933, Jul. 6, 1993, abandoned.

[51] Int. Cl.[6] .................................................... A61B 17/16
[52] U.S. Cl. ............................... 606/80; 606/79; 606/96; 606/98
[58] Field of Search ................................ 606/53, 54, 60, 606/79, 80, 81, 86, 87, 88, 95, 96

[56] References Cited

U.S. PATENT DOCUMENTS 5,129,909  7/1992  Sutherland .
5,176,684  1/1993  Ferrante et al. ........................... 606/86
5,417,695  5/1995  Axelson, Jr. .

FOREIGN PATENT DOCUMENTS

| 0 551 572 A3 | 7/1993 | European Pat. Off. ........ A61B 17/14 |
| 0 556 998 A1 | 8/1993 | European Pat. Off. ........ A61B 17/56 |
| 0 682 916 A2 | 11/1995 | European Pat. Off. ........ A61B 17/17 |
| 85 01914 | 2/1985 | France ............................... A61F 2/46 |
| 91 08139 | 6/1991 | France ........................... A61B 17/56 |

Primary Examiner—Jerome W. Donnelly
Assistant Examiner—Benjamin Koo
Attorney, Agent, or Firm—Todd A. Dawson

[57] ABSTRACT

The milling instrumentation of this invention provides a milling guide connected to the femur for accommodating a milling device. The milling instrumentation includes an alignment guide which is used by the surgeon to set a femoral bracket or base on the medial and lateral sides of the exposed femur adjacent its distal end. Once the brackets are set, the alignment guide is removed and a milling guide is connected to the bases. The milling guide establishes a series of reference planes each including a slot. A powered milling device having a burr connected thereto is guided by the slots along the reference planes to accurately mill away a portion of the bone. The milling device includes a bobbin-shaped tip which positively engages the slots to ensure that the milling device is held substantially perpendicular to the reference planes of the milling guide. If necessary, other instrumentation may be connected to the femoral bases which would form a common connection point for the additional instruments thereby ensuring alignment between the various instruments. Optionally, a one piece cutting guide may be connected to the bases to allow resection of the bone by a standard oscillating saw blade. The cutting guide includes a plurality of slots such that all the cuts required for the femur can be made with one cutting guide without reorienting the guide.

3 Claims, 17 Drawing Sheets

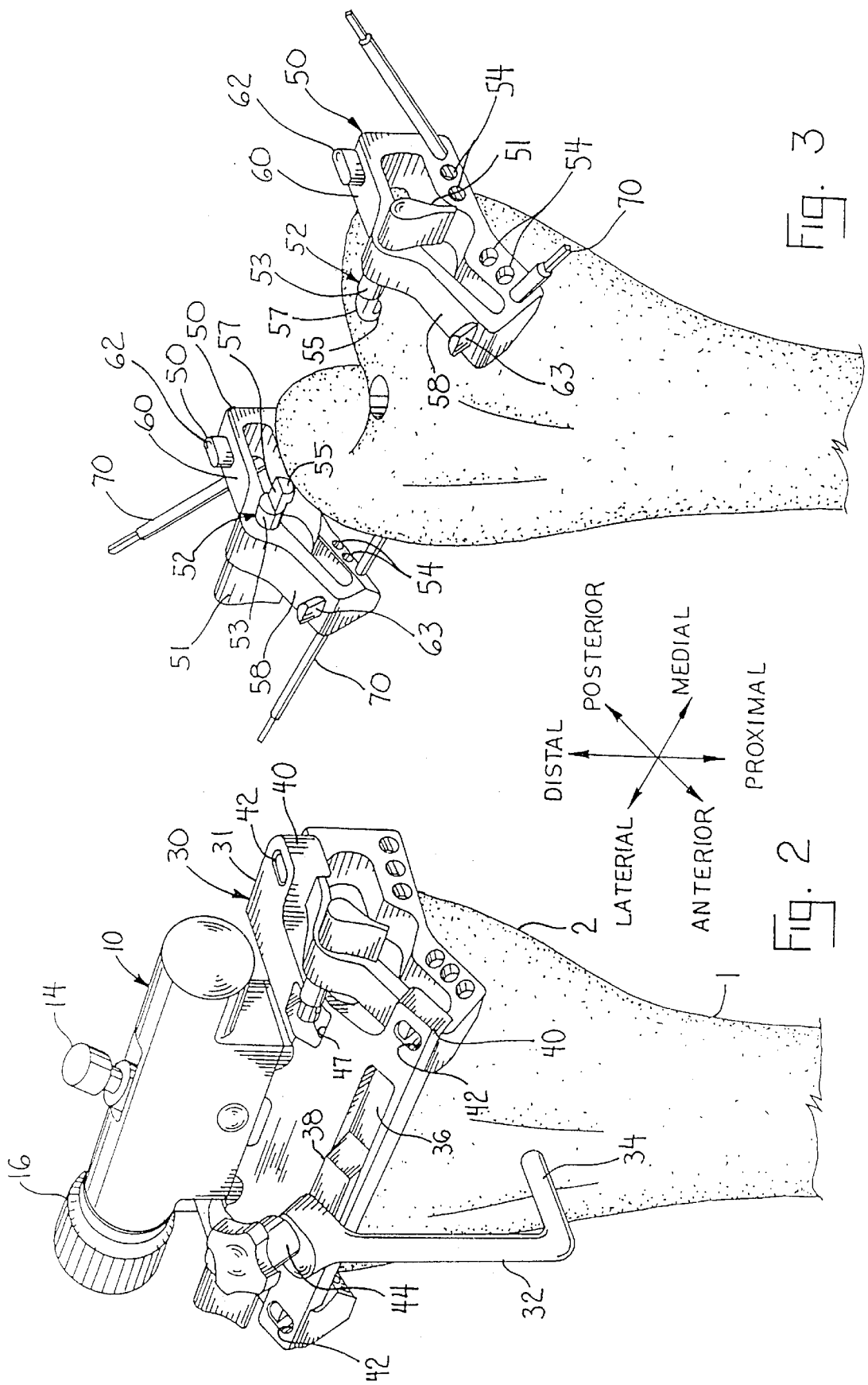

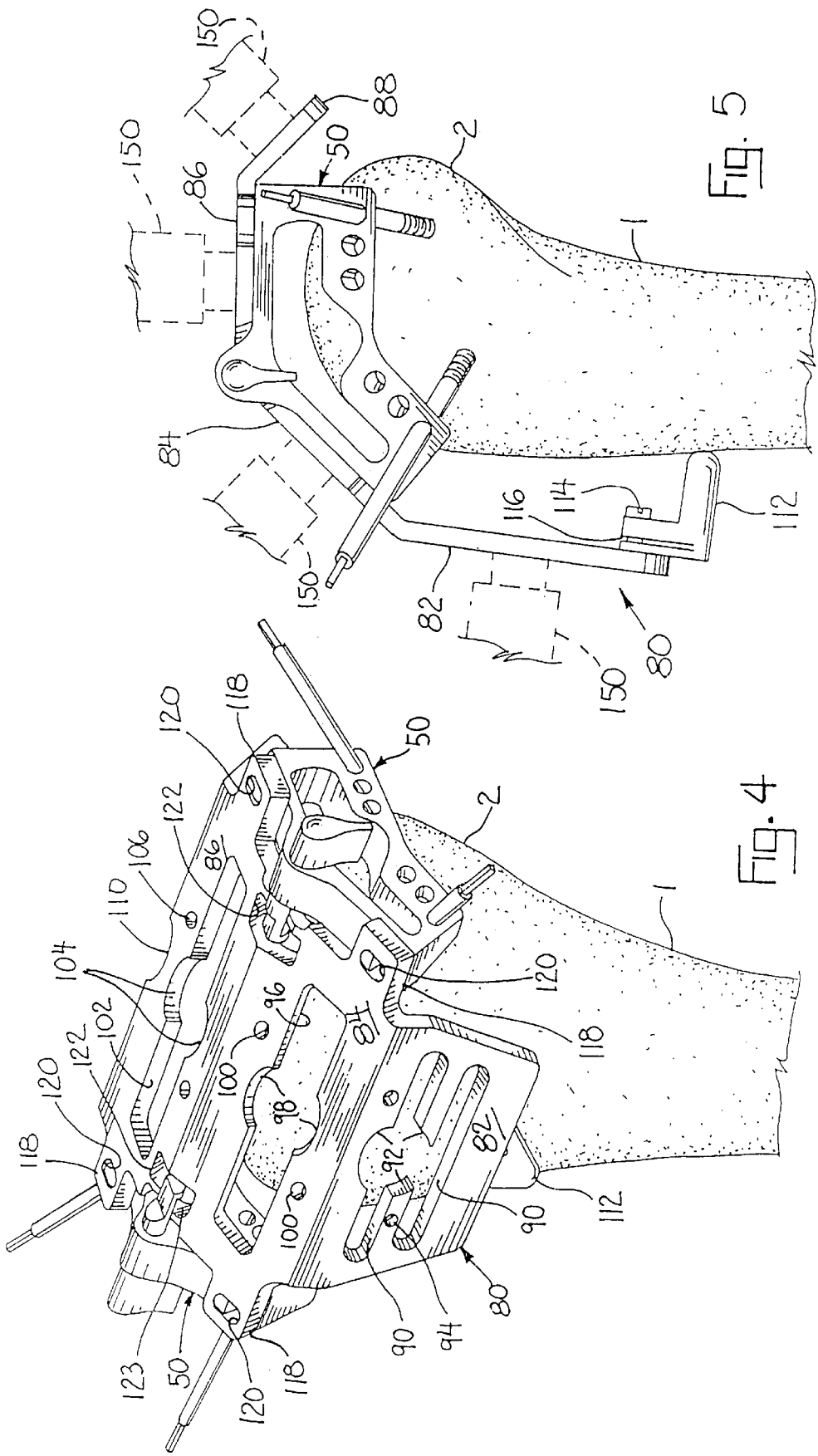

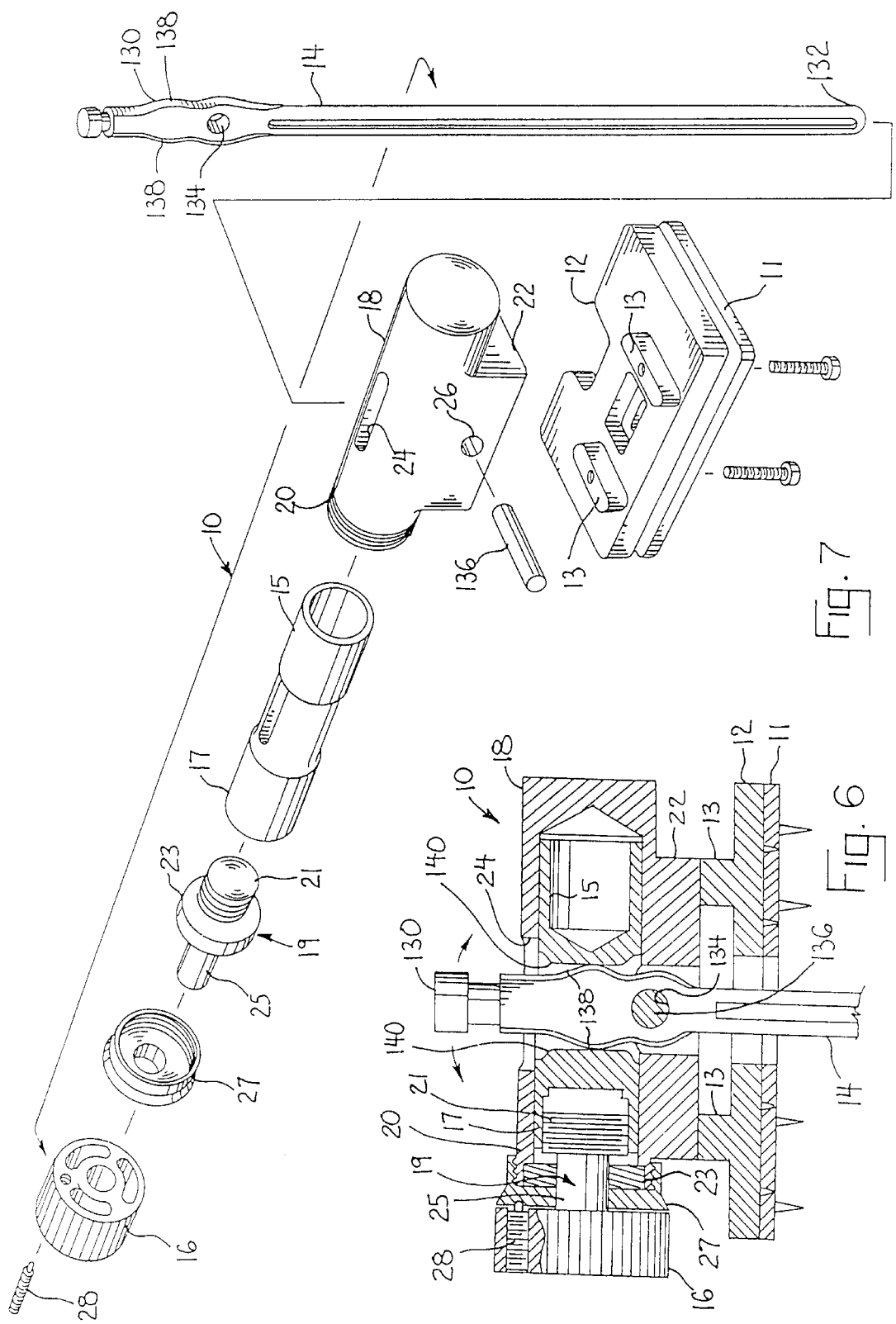

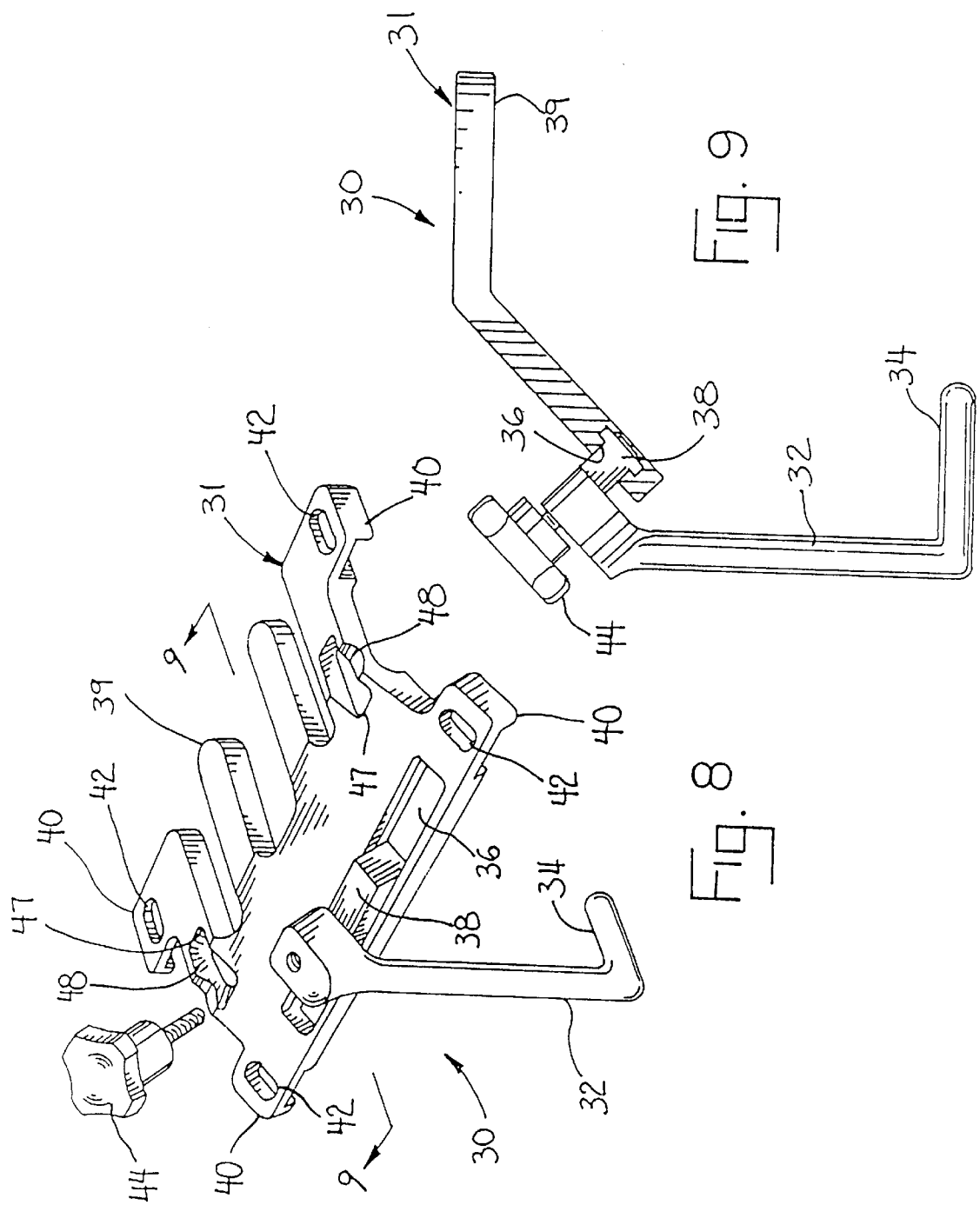

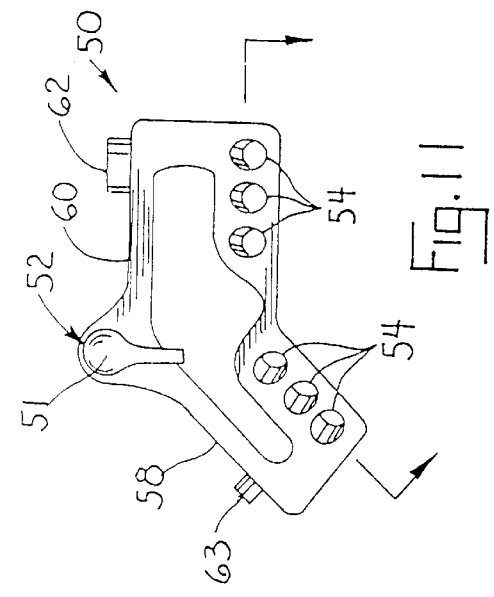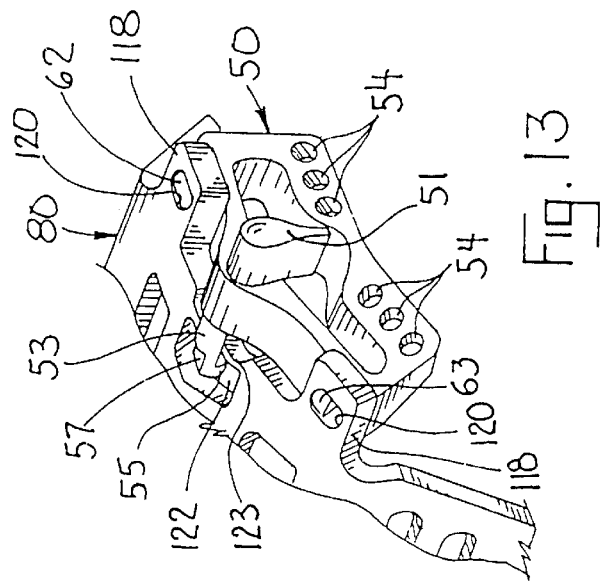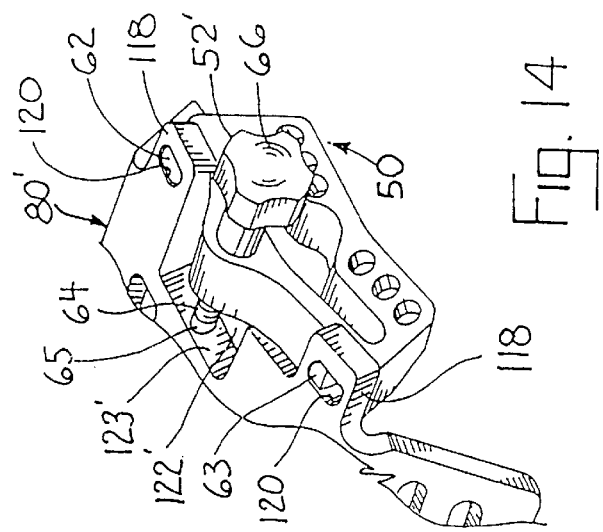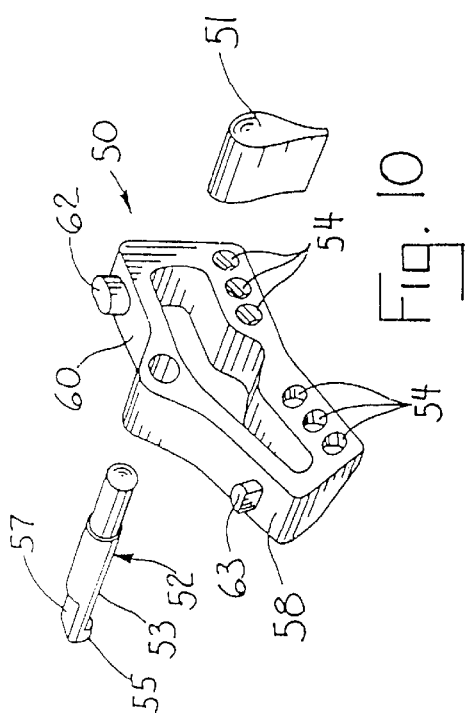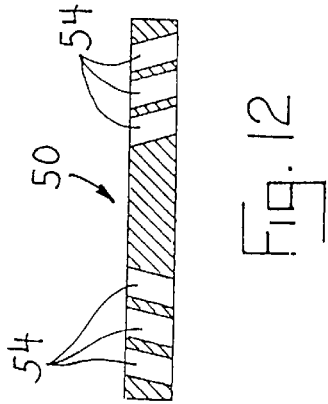

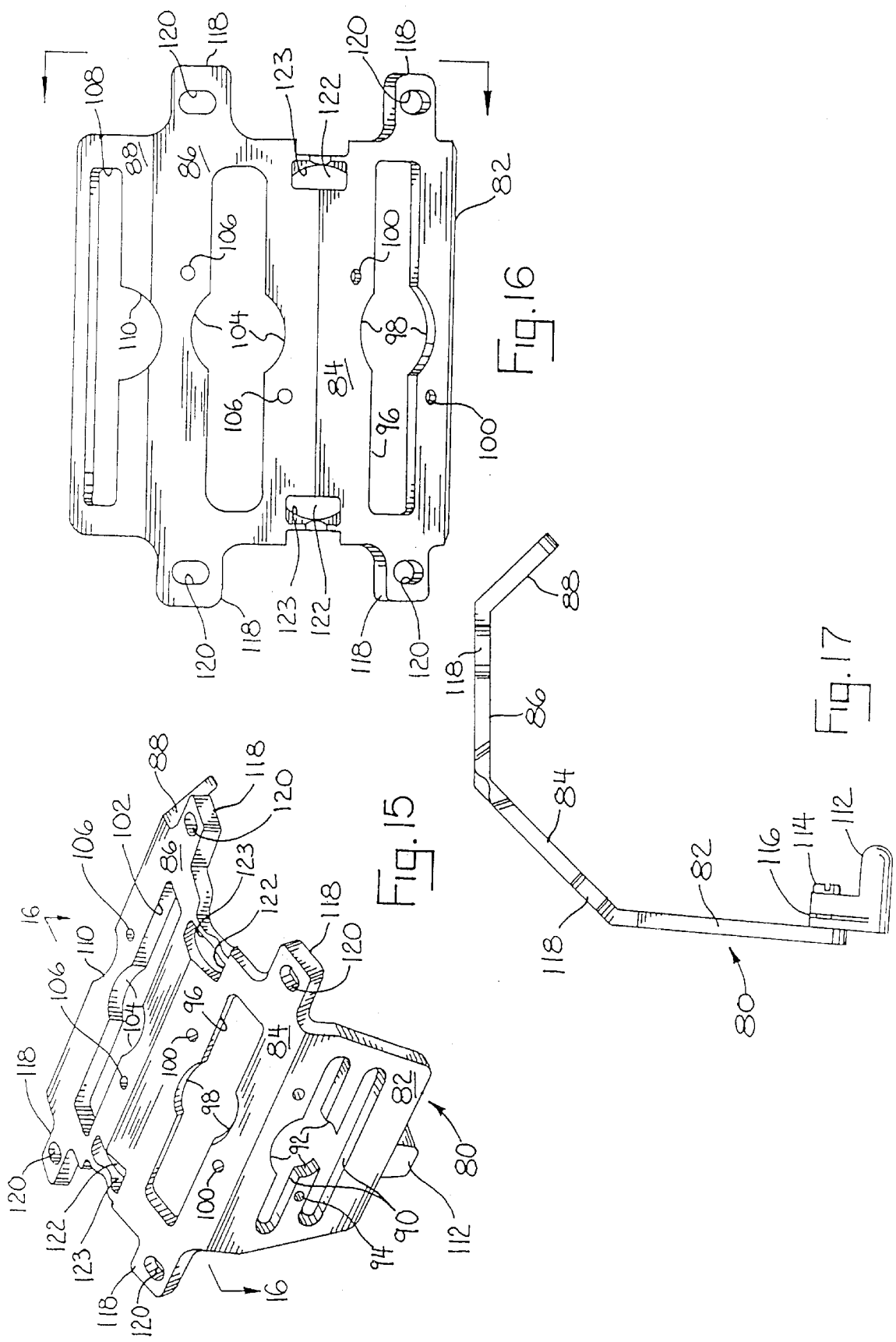

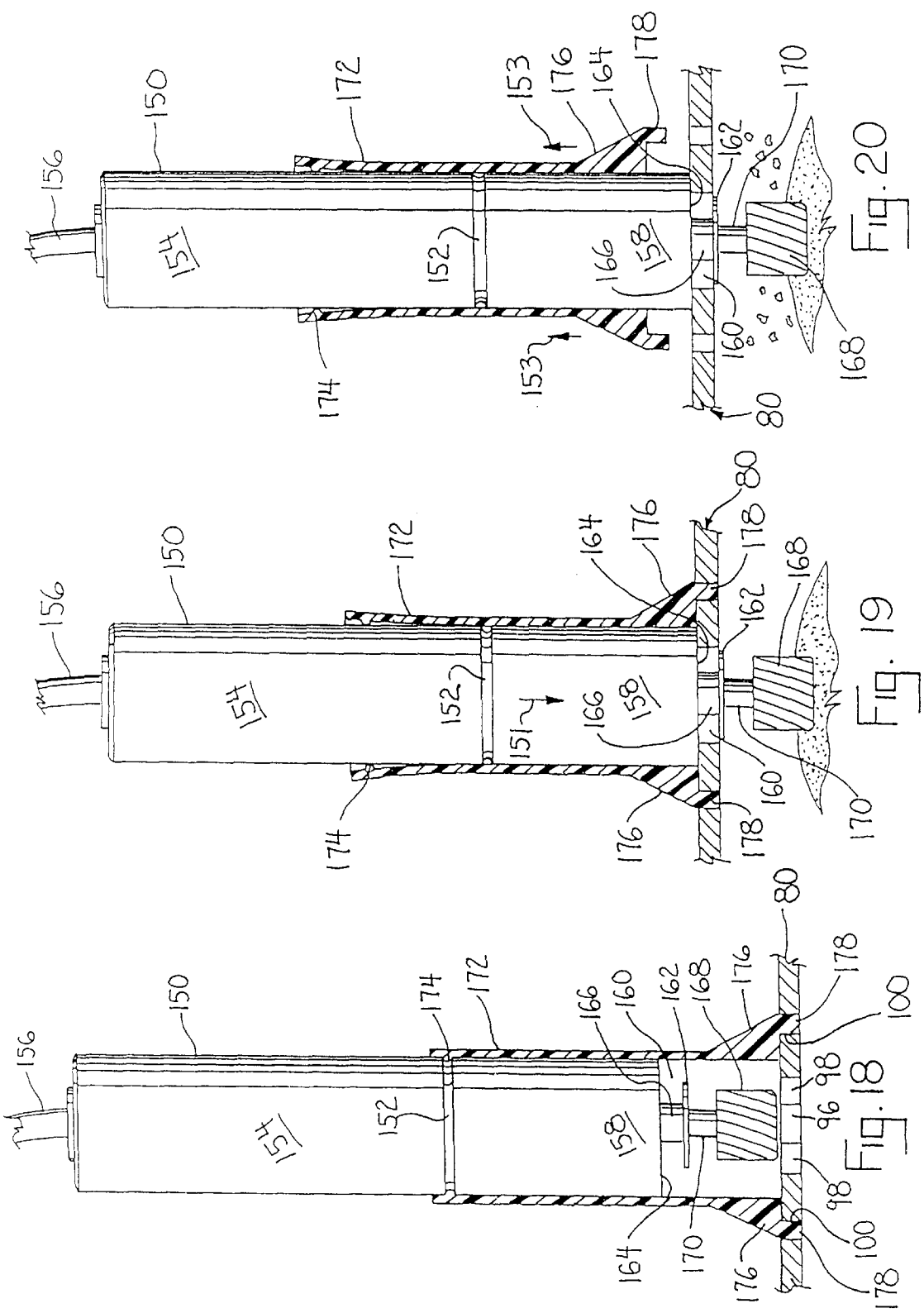

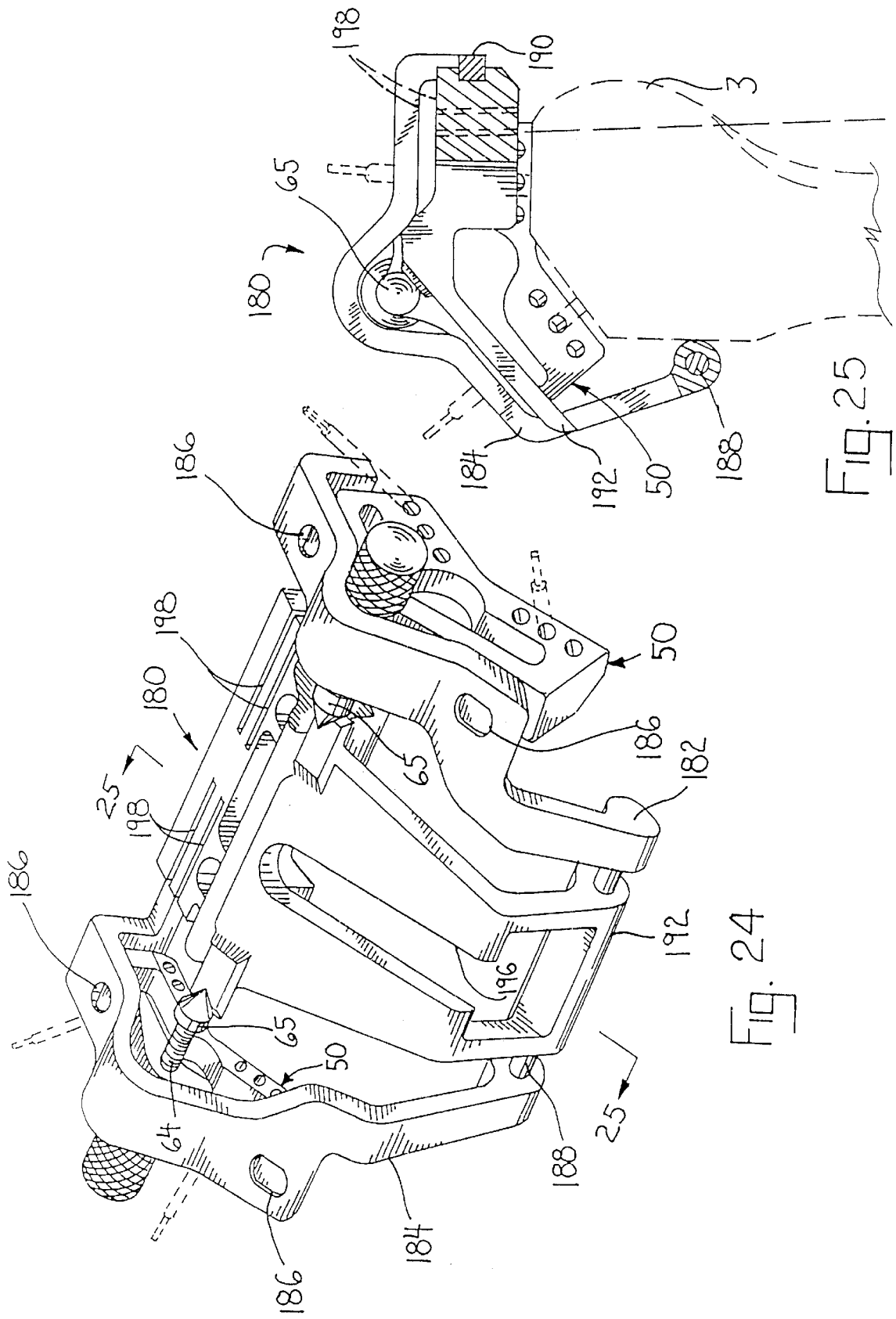

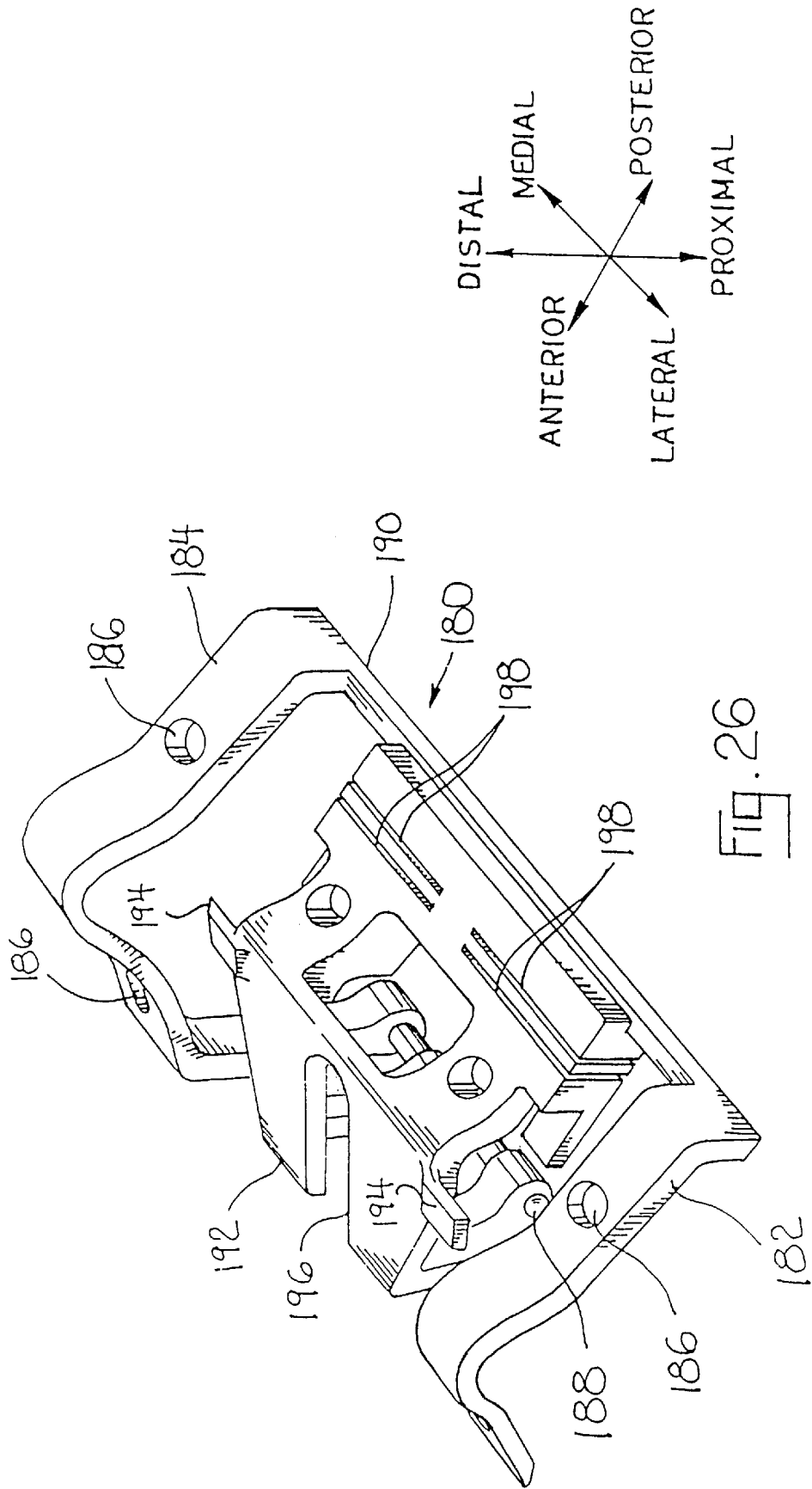

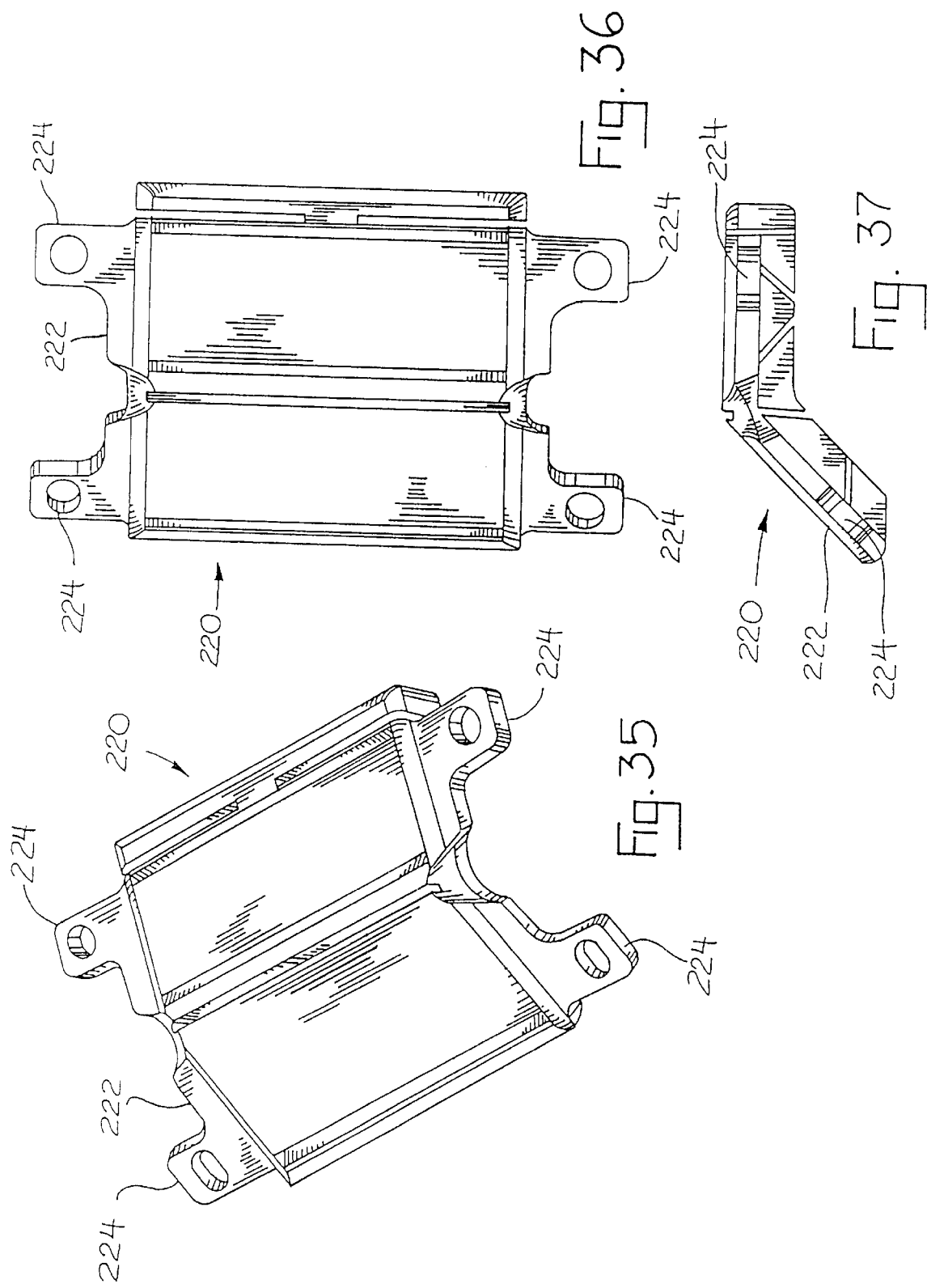

ously prepared by
FEMORAL MILLING INSTRUMENTATION FOR USE IN TOTAL KNEE ARTHROPLASTY WITH OPTIONAL CUTTING GUIDE ATTACHMENT This is a division of application Ser. No. 08/169,459 filed Dec. 17, 1993, now U.S. Pat. No. 5,474,559. Which is a CIP of 08/087,933, filed Jul. 6, 1993 now abandoned.

FIELD OF THE INVENTION

This invention relates to instruments used in the preparation of the femur during a total knee arthroplasty and has specific relevance to instrumentation providing for the milling of the femur while providing the option of resecting portions of the femur using a one piece cutting guide.

BACKGROUND OF THE INVENTION

In an orthopaedic surgery to replace part or all of a patient's joint with a prosthetic implant, a portion of the implant receiving bone is prepared to closely match the mating surfaces of the implant. If the knee joint is being replaced, the distal end of the femur is prepared to accommodate a femoral knee component and the proximal end of the tibia is prepared to accommodate a tibial component.

Heretofore, these surfaces were substantially prepared by the use of reciprocating or oscillating saw blades used in conjunction with a series of saw guides. The guides may comprise merely a platform on which the surgeon rests the blade during resection or may comprise a slot for capturing the saw blade therewithin. Typically, in the preparation of the femur, a series of cutting guides are placed adjacent the distal femur in a specific order to resect portions of the femur in succession. These cutting guides are generally individually aligned by the surgeon with reference to specific anatomic landmarks. The use of multiple cutting guides requiring individual alignment by the surgeon may lead to inaccuracies in the cuts which would provide a less than optimal fit between the bone and implant. Such saw blades commonly used in the resection of bone are illustrated in U.S. Pat. Nos. 5,002,555, 5,133,728, and 5,135,533. An example of a typical cutting guide may be had by reference to U.S. Pat. No. 5,053,037, illustrating a saw guide having captured slots.

The consistency of results achieved when using a saw blade and a series of cutting guides may vary widely from surgeon to surgeon.

SUMMARY OF THE INVENTION

The milling instrumentation of this invention solves the deficiencies of the prior art systems by providing a milling guide connected to the femur for accommodating a milling device. The milling instrumentation includes an alignment guide which is used by the surgeon to set a femoral bracket or base on the medial and lateral sides of the exposed femur adjacent its distal end. Once the brackets are set, the alignment guide is removed and a milling guide is connected to the bases. The milling guide establishes a series of reference planes each including a slot. A powered milling device having a burr connected thereto is guided by the slots along the reference planes to accurately mill away a portion of the bone. The distance between the milling device and the distal end of the burr is relatively short, and the shaft of the burr is stiff to thereby eliminate any deflection in the burr. Further, the milling device includes a bobbin-shaped tip which positively engages the slots to ensure that the milling device is held substantially perpendicular to the reference planes of the milling guide. Controlling the milling device in this manner ensures an extremely flat milled surface for accommodating the implant. If necessary, other instrumentation may be connected to the femoral bases which would form a common connection point for the additional instruments thereby ensuring alignment between the various instruments.

Optionally, once the femoral bases are connected to the distal end of the femur, a one piece cutting guide may be connected to the bases to allow resection of the bone by a standard oscillating saw blade. The cutting guide includes a plurality of slots such that all the cuts required for the femur can be made with one cutting guide without reorienting the guide. By making all the cuts required without moving the guide or requiring additional guides, the accuracy and repeatability of the cuts are increased.

Accordingly, it is an advantage of this invention to provide for novel milling instrumentation for preparing a bone surface to accommodate an orthopaedic implant.

Another advantage of the invention is to provide for milling instrumentation which includes an alignment guide for connecting a pair of brackets to an exposed bone.

Another advantage of the invention is to provide for milling instrumentation which includes a milling guide connected to a bone for guiding a milling device to prepare a surface of the bone for accommodating an orthopaedic implant.

Still another advantage of the invention is to provide for a novel milling device having a bobbin-shaped end for captured engagement within the slot of the milling guide.

Yet another advantage of the invention is to provide a base for connection to sides of a bone for connection of a plurality of milling devices.

Still another advantage of the invention is to provide for an instrumentation set for resecting bone that provides for the optional attachment of a cutting guide or a milling guide.

Still another advantage of the invention is to provide for a one piece cutting guide.

Additional advantages may be understood by a reading of the following description taken with the accompanying drawings.

BRIEF DESCRIPTION OF THE DRAWINGS

FIG. 2 is a perspective view of the alignment guide of FIG. 1 with the Anterior-Posterior (AP) placement guide connected thereto. The brackets of femoral bases are removably connected to the AP placement guide and are illustrated removably secured to the femur by a plurality of screws.

FIG. 3 illustrates the femoral bases connected to the femur by screws. The alignment guide and AP placement guide have been removed.

FIG. 4 is a perspective view of the femoral milling guide attached to the femoral bases on the distal end of the femur.

FIG. 5 is an elevational view of FIG. 4 with a milling device (partially shown) illustrated in broken lines to illustrate the relative position of the milling device, milling guide and distal femur.

FIG. 6 is a partial cross-sectional view of the alignment guide of the invention.

FIG. 7 is an exploded view of the alignment guide of the invention.

FIG. 8 is a perspective view of the AP placement guide shown in isolation and partially exploded.

FIG. 9 is a sectional view taken along line 9—9 of FIG. 8.

FIG. 10 is a perspective view of a femoral base shown in isolation and exploded for illustrative purposes.

FIG. 11 is an elevational view of a femoral base of the invention.

FIG. 12 is a cross-sectional view taken along line 12—12 of FIG. 11.

FIG. 13 is an enlarged partial view of a femoral base connected to a femoral milling guide illustrating the cam lock between the base and guide.

FIG. 14 is an enlarged partial view of a femoral base connected to a femoral milling guide illustrating an alternative screw and ramp locking mechanism.

FIG. 15 is an isolated perspective view of the femoral milling guide of the invention.

FIG. 16 is an elevational view taken along line 16—16 of FIG. 15.

FIG. 17 is a side elevational view of the femoral milling guide of FIGS. 15 and 16.

FIGS. 18 through 20 illustrate the use of the milling device of the invention including the use of the plunge cut alignment sheath.

FIG. 24 is the perspective view of FIG. 23 with the notch milling guide connected to the femoral bases.

FIG. 25 is a side elevational view illustrating the notch milling guide of FIG. 24 connected to a resected distal end of a femur by the femoral bases.

FIG. 26 is a perspective view of the notch milling guide of FIG. 23 shown from the posterior side.

FIG. 35 is a perspective view of the one piece cutting guide.

FIG. 36 is a elevational view of the one piece cutting guide.

FIG. 37 is a side elevational view of the one piece cutting guide.

Figure 1:
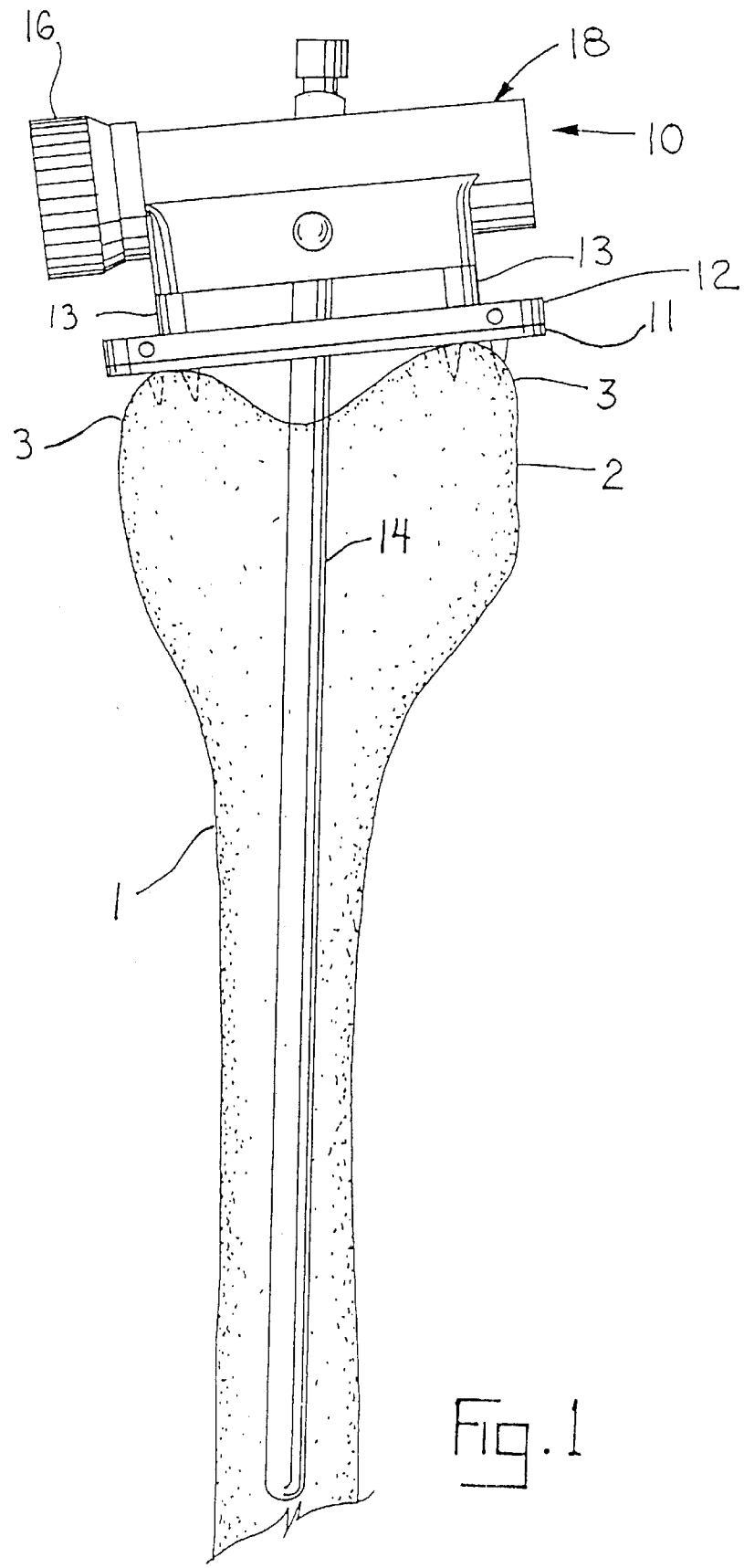
FIG. 1 is an elevational view illustrating the alignment guide of the invention inserted into the intramedullary canal of a distal end of the femur.

To illustrate the orientation of the instruments shown in the drawings and herein described, a small compass is illustrated on many drawings demonstrating orientation of the instrument with reference to the relative anatomical axes of the femur as are well understood in orthopaedics.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Initially, after the distal end 2 of the femur 1 is exposed consistent with standard surgical techniques, the surgeon forms an intramedullary hole into the center of the distal femur in a known manner to accommodate an intramedullary device. The femoral intramedullary alignment guide 10 is inserted into the intramedullary hole until the platform 12 of the alignment guide 10 contacts the distal condyles 3, 4 as shown. As illustrated, the platform 12 may be angled relative to the intramedullary rod 14 to allow the surgeon to align the platform 12 perpendicular to the mechanical axis of the femur 1. The method of angulating the rod relative to the platform is explained below.

An Anterior-Posterior alignment guide 30 (hereafter AP guide 30) having femoral bases 50 temporarily attached thereto is slid onto alignment guide 10. AP guide 30 includes an arm 32 which is shiftable in the medial-lateral direction of the femur. Arm 32 terminates in a posteriorly extending projection 34. The surgeon adjusts arm 32 such that projection 34 is in contact with the highest anterior point of the anterior femoral condyle. The AP guide 30 is shiftable in an anterior-posterior direction relative to alignment guide 10 and the femur for proper positioning of arm 32 as explained above. Once the surgeon is satisfied with position of AP guide 30, a plurality of tapered bone screws 70 are inserted through openings 54 in femoral bases 50 as illustrated to secure the bases to the medial and lateral sides of the femur. Once the bases 50 are secured to the femur, the AP guide 30 and alignment guide 10 may be removed by disengaging locking mechanisms 52 thereby freeing the AP guide. Alignment guide 10 and AP guide 30 are removed leaving only bases 50 connected to femur 1 as illustrated in FIG. 3. The specific design and operation of the locking mechanisms. 52 of femoral bases 50 is described later in the specification with reference being had to FIGS. 10 through 14.

After the AP alignment guide 30 and alignment guide 10 are removed, a generally C-shaped femoral milling guide 80 (see FIGS. 4 and 5) is placed onto bases 50 and secured thereto by locking mechanisms 52. FIGS. 4 and 5 illustrate the milling guide 80 in its environment connected to femoral bases 50 and the femur 1. FIGS. 15 through 17 illustrate the milling guide alone so that its design might be more clearly understood. Milling guide 80 is shaped so as to form a plurality of generally flat walls lying in a like plurality of planes which are identified relative to the femoral surfaces to be milled. Guide 80 includes a femoral anterior wall 82, an anterior chamfered wall 84, a distal wall 86 and a posterior chamfered wall 88 each having upper and lower surfaces as illustrated in FIGS. 4, 5 and 15–17. Anterior wall 82 includes a pair of generally parallel slots 90 configured as shown for accommodating and guiding a milling device along the anterior surface of the femur for milling the anterior femoral condyle 4 of femur 1. An arcuate opening 92 is formed in one slot 90, as illustrated, which places slots 90 in communication with one another as illustrated. A pair of through bores 94 are formed on opposite sides of arcuate opening 92. Anterior chamfer wall 84 includes a slot 96 having facing arcuate interruptions 98 formed in the side walls of the slot 96 as illustrated. Slot 96 is formed to accommodate and guide a milling device along the femur 1 to form an anterior chamfer surface 6 on the femur (see FIG. 5). A throughbore 100 is formed adjacent each arcuate interruption 98. Distal wall 86 includes a slot 102 having facing arcuate interruptions 104 formed in the side walls of the slot 102. Slot 102 is formed to accommodate and guide a milling device along the femur to form a prepared distal surface 8 on the femur (see FIG. 5). A throughbore is formed adjacent each arcuate interruption 104. Posterior chamfer wall 88 includes a slot 108 having an arcuate projection 110 formed in the anterior most side wall of the slot as illustrated best in FIG. 16. A generally L-shaped support 112 is rotatably connected to the posterior surface of the anterior femoral wall 82 by a screw 114 passing through the foot of the support. The leg of the support extends away from the anterior femoral wall 82 and is configured to contact the anterior cortex of femur 1 just proximal to the anterior condyles 4. A slot 116 is cut into the foot of the support to create a spring out of the foot. In use, the surgeon rotates the support about screw 114 until the distal tip of the leg contacts the highest point on the anterior cortex of the femur adjacent the anterior condyles. The spring formed from the foot provides sufficient spring effect to allow the support to be placed into position with a degree of force thereby providing additional stability to the anterior condyle wall 82 of milling guide 80. A tab 118 extends from the medial and lateral sides of the anterior chamfer wall 84 in a plane therewith and includes an ovoid opening 120. Similarly, a tab 118 extends from the medial and lateral edges of the distal surface 86 in a plane therewith and includes an ovoid opening 120 therethrough. An opening 122 is formed adjacent the medial and lateral edges of femoral milling guide 80 between the anterior chamfer wall 84 and the distal wall 86. The outermost side walls 123 of openings 122 are inclined inwardly and angled posteriorly so as to form a ramp-like structure for engagement by the locking mechanism 52 of femoral base 50 as explained below.

FIG. 5 is provided to illustrate the relative position of the femoral base 50 and the milling guide 80 in relationship to the exposed femur 1. A milling device is shown in broken lines positioned at each wall 82, 84, 86, and 88 for illustrative purposes. In use, a burr would extend down to the bone for shaping bone as explained below. In combination, the milling device as guided by the milling guide 80 of the invention would allow the surgeon to resect, by milling, the anterior femoral condylar surface 4, the anterior chamfer surface 6, the distal surface 8 and the posterior chamfer surface 9 in a series of milling steps without changing or attaching additional instruments to the femur 1. The milling guide 80 provides for the milling of the four mentioned surfaces without additional set up or guides from a single reference established by the femoral bases 50.

Alignment guide 10 is illustrated in more detail in FIGS. 6 and 7. With reference to FIGS. 6 and 7, alignment guide 10 includes a hollow housing 18 which is generally cylindrical in shape and is open at one end 20. Housing 18 further includes a base 22 extending laterally from the generally cylindrical portion of the housing. An elongated opening 24 is formed through the housing as illustrated along the longitudinal dimension of the housing. A throughbore 26 is formed through base 22 in communication with opening 24 and transverse thereto. External helical threads are formed on the housing 18 adjacent its open end 20. Platform 12 includes a pair of legs 13 extending therefrom as illustrated and is secured to base 22 by screws. Platform 12 further includes a spacer 11 which may be selectively attached to the platform by screws. Platform 12 and spacer 11 include central openings for accommodating the intramedullary rod 14 therethrough. Legs 13 define an opening between the platform 12 and the base 22 for accommodating portions of the AP alignment guide 30.

A generally cylindrical cam 15 is provided and is accommodated within housing 18 in a close fit thereto. Cam 15 is longitudinally slidable within housing 18. An elongated opening is formed through cam 15 for alignment with opening 24 of housing 18 when the cam is positioned within housing 18. Each longitudinal end of cam 15 is bored out with end 17 including internal helical threads. A coupler 19 having a longitudinal shaft with a threaded end 21 and an annular collar 23 is provided. Threaded end 21 is accommodated by the threaded end 17 of cam 15 and is rotatable therewithin. Collar 23 is received within a counter bore formed in end 20 of housing 18 as illustrated in FIG. 6. An end cap 27 having a central opening is threaded onto end 20 of housing 18 and captures collar 23 against longitudinal movement relative to housing 18. Knob 16 is press fitted onto the non-threaded end of coupler 19 such that as knob 16 is rotated relative to the housing, coupler 19 rotates relative to cam 15. A detent 28 is accommodated within a threaded through bore within knob 16 and includes a spring-loaded nib to engage the end face of end cap 27. A plurality of grooves (not shown) may be formed in the end face of end cap 27 for successive engagement with the nib to provide a positive snap feel to the knob as well as to indicate the relative position of the knob.

An intramedullary rod 14 is provided and includes a proximal end 130 and a distal end 132. The proximal end includes an annular recess for accommodating a griping device for the removal of the alignment guide 10 from the intramedullary canal of the femur. A transverse through bore 134 is formed through rod 14. As illustrated, rod 14 is pivotally secured within the opening 24 and the aligned opening of cam 15 by a pin 136. As is further illustrated, a portion of the proximal end 134 of the rod 14 is flattened and defines caming surfaces 138.

In use, the surgeon varies the angle between intramedullary rod 14 and platform 12 so that platform 12 is perpendicular to the mechanical axis of the femur by rotating knob 16 relative to housing 18. The rotation of knob 16 causes coupler 19 to rotate within cam 15. Cam 15 is rotationally fixed relative to housing 18 and coupler 19 is longitudinally fixed relative to housing 18. Therefore, when knob 16 rotates coupler 19, the threaded engagement between coupler 19 and cam 15 causes the cam to longitudinally shift within housing 18. The longitudinal movement of cam 15 causes a cam surface 140 of cam 15 to press against a cam surface 138 on rod 14 thereby causing rod 14 to rotate about pin 136 thereby angulating rod 14 relative to platform 12. Indicia may be provided on knob 16 to indicate to the surgeon the relative angle between the rod and platform.

AP alignment guide 30, shown isolated in FIGS. 8 and 9, includes a body, 31 having a plurality of fingers 39 extending therefrom. The innermost pair of fingers are adapted for accommodation within the spaces created by legs 13 of alignment guide 10 (see FIGS. 2 and 6). An inverted T-shaped channel 38 extends in a medial-lateral direction adjacent an anterior edge of the AP alignment guide as illustrated. An inverted T-shaped block is slidably accommodated within channel 38 and includes an arm 32 adapted to extend in the direction of the proximal end of the femur (see FIG. 2). A posteriorly extending projection 34 extends from arm 32. A tab 40 extends transversely from the distal end of each of the outermost fingers 39 and includes an ovoid opening 42. Similarly, a tab 40 extends from the medial and lateral edges adjacent the anterior edge of body 31 and includes an ovoid opening 42 as illustrated. Each tab 40 includes a channel 46 for accommodation of the femoral bases 50 therein. A set screw 44 having an enlarged head is accommodated within a threaded bore in block 38. Screw 44 may be rotated into engagement with the bottom wall of T-channel 36 to temporarily fix the block from movement within the channel. An opening 47 is formed adjacent the medial and lateral edges of alignment guide 30 between the body 31 and finger 39. The outermost side walls 48 of openings 47 are inclined inwardly and angled posteriorly so as to form a ramp-like structure for engagement by the locking mechanism 52 of femoral base 50.

The femoral base 50 of the invention is illustrated in FIGS. 2–5 and 10–13 with an alternative embodiment illustrated in FIG. 14. In practice, two femoral bases 50 are required; however, only one need be described here as the two bases in use are simply mirror images of one another. Femoral base 50 includes a body 56 defining a substantially flat anterior distal surface 58 and a substantially flat posterior distal surface 60. The body 56 is curved slightly such that the surfaces 58 and 60 are not in the same plane. Locking mechanism 52 is situated between surfaces 58 and 60 and includes a bore extending transversely through the body, a cam bar 53 extending through the bore and a handle 51 connected to an end of bar 53 which extends laterally from the body. The medial end of the cam bar 53 includes a small cam 55 extending transversely to the cam bar. A portion of cam bar 53 is removed to form a relief 57 adjacent the cam 55. An ovoid protuberance 62 extends in a distal direction from posterior distal surface 60 and a semi-circular protuberance 63 extends in a distal direction from the anterior distal surface 58 as illustrated in the drawings. As mentioned earlier and as illustrated in the drawings, femoral base 50 includes a plurality of openings 54. Three openings 54 are positioned anteriorly and three are positioned posteriorly on the body 56. As illustrated best in FIGS. 11 and 12, the anterior openings 54 are angled such that a screw passing therethrough is directed proximally and posteriorly within the bone. The posterior openings 54 are angled such that a screw passing therethrough is directed proximally and anteriorly within the bone. Therefore, if screws are inserted through at least one anterior opening and at least one posterior opening on the body 56, the screws converge toward each other to thereby securely lock the femoral base 50 to the bone. Preferably, the diameter of the shaft of the screw passing through the body opening should closely match diameter of the openings 54 to assist in the mechanical interlock being formed.

The operation of the locking mechanism 52 is illustrated in FIG. 13. As mentioned, mechanism 53 includes a relief 57 and a cam 52 formed in cam bar 53 which is rotatable relative to body 56. Connecting and disconnecting the base 50 with locking mechanism 52 is accomplished in the same manner whether the base is being connected to AP alignment guide 30 or milling guide 80 and will therefore only be described in relation to AP guide 30. To connect a base 50 to AP guide 30, the protuberances 62, 63 are aligned and seated within ovoid openings 42 of a pair of tabs 40. To permit the base 50 to fully seat against the tabs 40, cam bar 53 is slid in a direction away from the AP guide 30. To lock the base to the guide, cam bar 53 is rotated using handle 51 until the relief 57 is facing the AP guide 30. Bar 54 is slid toward the AP guide 30 until the cam 55 is in general alignment with opening 47 of the AP guide. The bar 53 is then rotated such that cam 55 enters opening 47 and contacts the inclined wall 48. Continued rotation causes cam 55 to press against the inclined wall 48 to thereby clamp the base 50 to the AP guide 30. To disengage base 50 from the guide, the cam bar 53 is rotated such that the cam 55 moves away from the inclined wall 48.

An alternative embodiment of the locking mechanism is illustrated in FIG. 14. In the alternative embodiment, locking mechanism 52' includes a screw 64 threadably accommodated by base 50 and including at one end a smooth conical tip 65 and a knob 66 at the other end. The guide 30' includes an opening 47' which includes an inclined wall 48'. In use, to lock the guide 30' to base 50', screw 64 is rotated until its conical tip 65 contacts the inclined wall 48' to clamp guide 30' between the tip 65 and base 50'.

A milling device 150 for use with the femoral milling guide 80 is illustrated in FIGS. 18 through 20 in association with a portion of guide 80. Milling device 150 includes a driver, a generally cylindrical housing 154 and being connected to an external energy source (not shown) by cord 156. As is well known in the industry, the external energy source could be pressurized gas or an electrical power source. The end of the housing terminates in a bobbin-shaped nose portion 158 as illustrated more clearly in FIG. 22. The bobbin shape of the nose portion 158 defines a predetermined spacing 160 between plate 162 and the end 164 of the housing which are interconnected by a tubular shaft 166. A burr 168 having a shaft 170 is attached to the milling device 150 using a known chuck to securely clamp the burr to the device 150. Milling device 150 rotates burr 168 in use. Burr 168 may also be referred to as an end cutter and has a end face which is substantially perpendicular to the burr shaft. A sleeve 172 is carried by housing 154 and is slidable longitudinally along the housing between an extended position as illustrated in FIG. 18 and a retracted position as illustrated in FIG. 20. Sleeve 172 is generally cylindrical and shaped to frictionally engage the outer surface of the housing 154. An annular rib 174 is formed adjacent one end for seating within an annular groove 152 on housing 154 as illustrated in FIG. 18. Rib 174 and groove 152 combine to form a detent to frictionally retain the sleeve in the extended position of FIG. 18. When the sleeve is retracted, the end adjacent the rib 174 yields slightly as illustrated; therefore, one or more slots may be formed in the sleeve to prevent its breaking when in a retracted position. A pair of shoulders 176 extend outwardly from the cylindrical portion of sleeve 172 adjacent one end and each includes a protrusion 178 extending parallel to the longitudinal axis of the sleeve.

Figure 22:
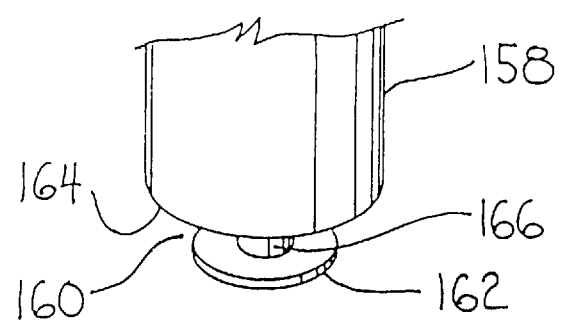
FIG. 22 illustrates a partial perspective view of the milling device illustrating the bobbin-shaped end of the milling housing.
Figure 27:
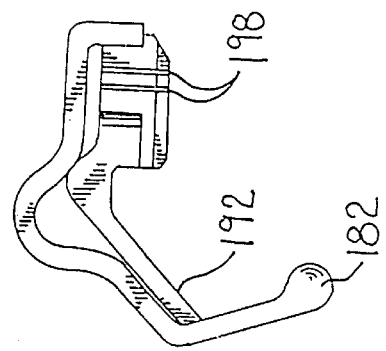
FIG. 27 is a side view taken from line 27—27 of FIG. 23.
Figure 23:
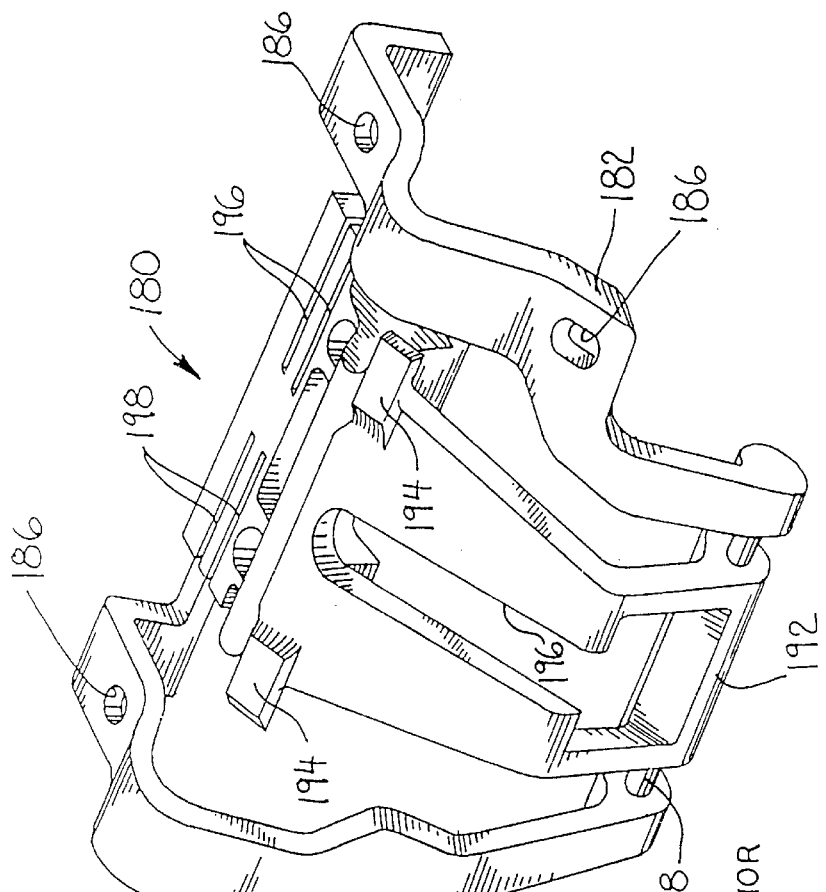
FIG. 23 is a perspective view of a notch milling guide which is connectable to the resected femur and guides a milling device for forming a notch in the distal femur. The notch is called for when the implant to be fitted to the femur includes mechanisms intended to restrain motion of the knee such as in a constrained condylar implant.
Figure 28:
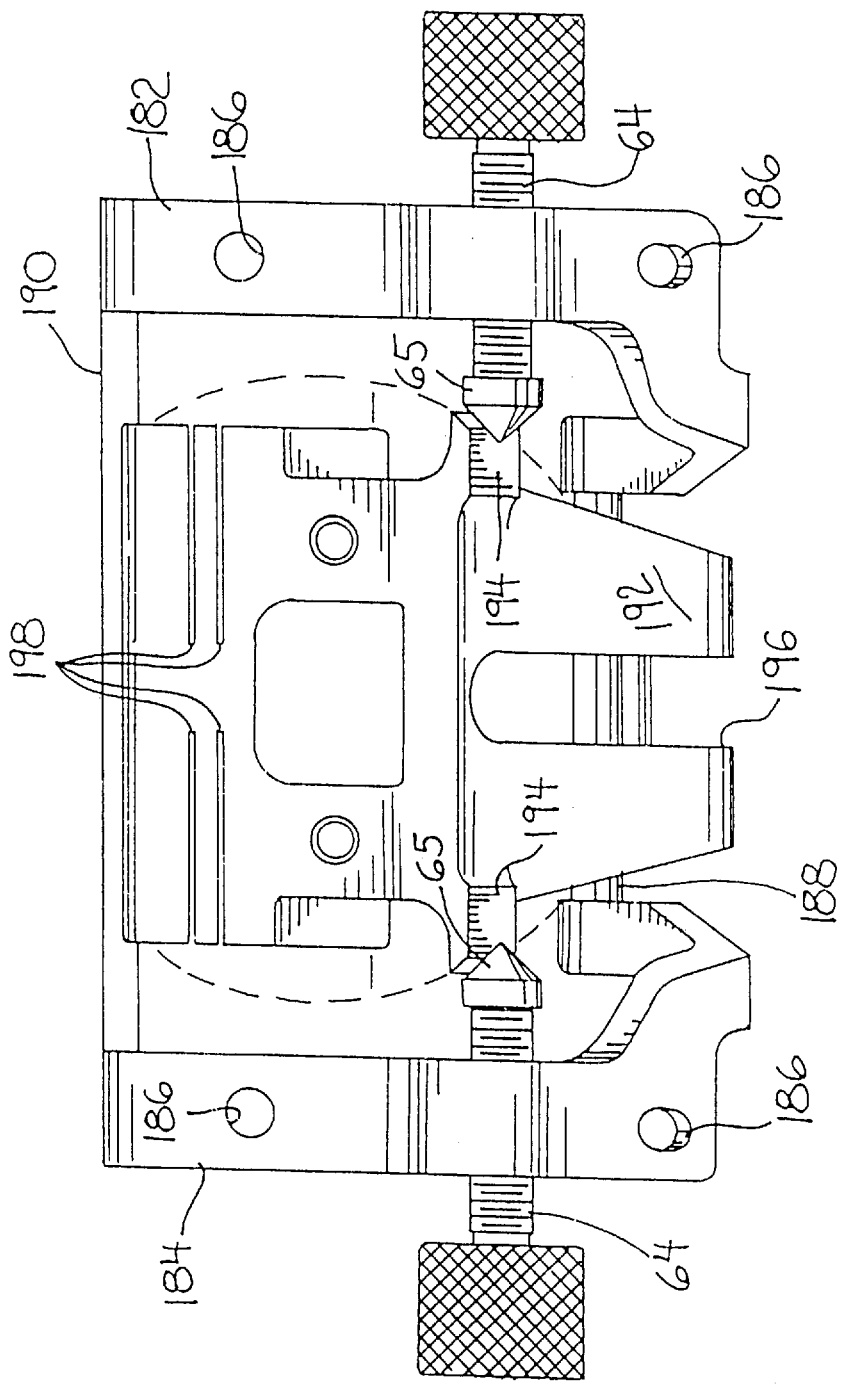
FIG. 28 is an elevational top view of the notch milling guide of FIG. 24.

In use, sleeve 172 serves two functions. Foremost is safety. Before the milling device is seated on guide 80, the surgeon and other operating room personnel are protected from the sharp edges of the burr by sleeve 172 in its extended position. The sleeve 172 also serves to align the milling device 150 and burr 168 for a plunge cut into the bone's surface. As mentioned earlier in the description of milling guide 80, the slots 90, 96, 102, and 108 of the guide each include arcuate portions 92, 98, 104, and 112 respectively. These arcuate portions or interruptions in the slots permit the milling device and burr to be inserted perpendicular to their respective walls. Sleeve 172 provides proper alignment between the arcuate sections and the burr so that as the burr rotates around its shaft and is lowered into milling engagement with the bone, the burr does not contact the guide. This alignment is accomplished by positioning protrusions 178 in the various through bores formed adjacent the arcuate portions of the slots. For example, referring to FIG. 18, protrusions 178 are positioned within through bores 100 so that the burr 168 is aligned with arcuate interruptions 98 of slot 96. Once properly aligned, the surgeon activates milling device 150 to rotate burr 168 and then gently pushes the milling device in the direction of arrow 151. Pushing the milling device 150 in the direction of arrow 151 unseats rib 174 from groove 152 thus allowing the burr be lowered into milling engagement with the bone as shown in FIG. 19. Also of importance at this point, it should be noted that the nose portion 158 of the milling device is aligned with the guide 80 such that the walls forming the slot are captured between plate 162 and end 164. To permit the milling device and burr to be guided by the surgeon over the entire length of the slot, the sleeve 172 is pulled in the direction of arrows 153 by the surgeon to disengage the protrusions from the through bores as illustrated in FIG. 20. With the sleeve in the retracted position of FIG. 20, the surgeon may guide the milling device along the slot for milling the entire surface of the bone. As mentioned, the bobbin shaped nose portion 158 of the milling device engages the slots to ensure that the milling device and burr are maintained substantially perpendicular to the particular wall of the milling guide 80. Maintaining the perpendicular relationship is vital to provide a very flat milled surface to accommodate the implant. A perspective view of the nose portion 158 of the milling device is illustrated in FIG. 22 in isolation.

Figure 21:
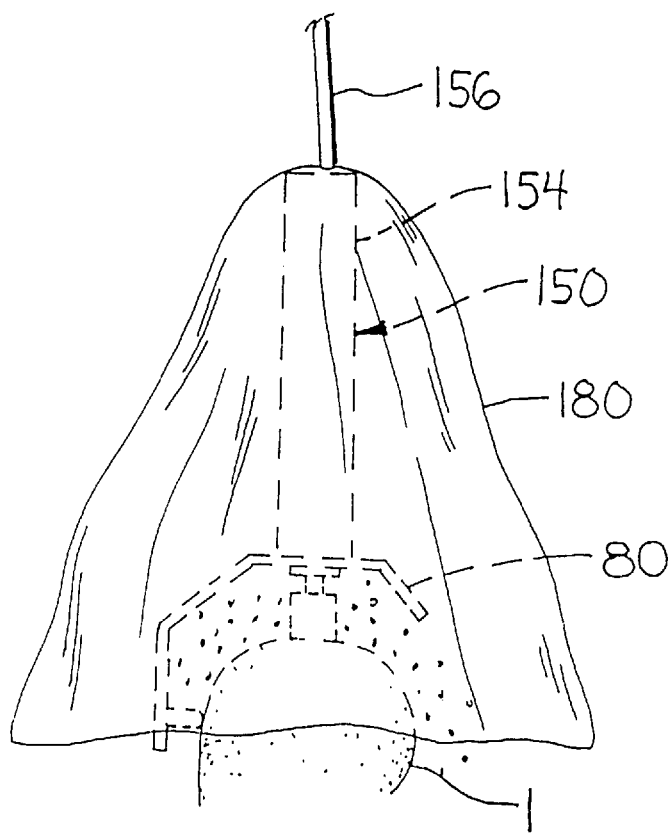
FIG. 21 illustrates the milling of the distal femur using the milling guide and device of this invention with the debris shield in place over the milling device.

FIG. 21 illustrates a protective sheet 180 which may be used during surgery to contain the particulate debris formed by milling the bone to the surgical site. Sheet 180 is translucent so that the surgeon's view of the milling process is not interrupted. The sheet may have an external. periphery of a number of shapes and includes a central opening to accommodate the cord 156 of milling device 150. Preferably, the sheet 180 is very limp and conforms easily to its surroundings to entrap as much of the bone debris as possible. In use, the surgeon's hands are positioned under sheet 18 and are grasping the milling device 150. Therefore, the sheet 180 provides a barrier to prevent debris from escaping the surgical site but does not create an impediment to the surgeon during the surgical procedure. The sheet 180 is positioned on the milling device 150 before the removable cord 156 is connected to the housing 154.

Depending on the type of femoral implant to be accommodated by the femur, the surgeon may be required to form a notch in the distal end of the resected bone. Typically this is required to accommodate implants referred to as constrained condylar knees and posterior stabilized knees. In these instances, generally the posterior and/or anterior cruciate ligaments of the knee are not functioning properly or have been removed as determined by the surgeon. The implant is therefore required to replace the functions of the ligaments. To do so, it is common for the femoral implant to include some type of protrusion which extends upwardly from the tibial plate and into the femur. To accommodate such an implant, a notch must be formed in the distal femur.

Notch milling guide 180, illustrated in FIGS. 23–28, is provided with the instrument set of the invention and includes sides 182, 184 which are shaped to conform with the upper surfaces of bases 50 and have openings 186 for accommodating protuberances 62, 63 of the bases. A bar 88 extends between the anterior most ends of sides 182, 184 and a bar 190 extends between the posterior most ends of sides 182, 184 to maintain the sides in a spaced relationship as illustrated. A guide body 192 is carried by bars 188, 190 and is shiftable on the bars between sides 182, 184. Guide body 192 includes a pair of tabs 194 which extend in opposition to each other. Tabs 194 are provided for engagement with conical tips 65 of screw 64 as carried by the femoral base 50 illustrated in FIGS. 14 and 24. Body 192 further includes a closed end slot 196 extending posteriorly. Slot 196 is configured to accommodate the bobbin shaped nose portion 158 of the milling device 150 in a similar manner as is illustrated in FIGS. 18–29. A series of slots 198 are formed adjacent the posterior edge of body 192 and adjacent bar 190 as illustrated in FIG. 26. Slots 198 are configured to accommodate an oscillating saw blade (not shown) for the resection of the posterior condyles 9 (see FIG. 25). In use, the surgeon places notch milling guide 180 on bases 50 and slides the guide body 192 medially and laterally on bars 188, 190 until an equal amount of the femur can be seen on each side of guide body 192 (see FIG. 28). This allows the surgeon to place the notch in the desired location relative to anatomical landmarks. Screws 64 are then turned until the conical tip 65 of each screw contacts a tab 194. The screws are then tightened against the tabs. Each screw 64 places a lateral force on a tab 194 in the direction of the other screw 64. Therefore, with each screw 64 tightened, guide body 192 is secured against a medial-lateral movement along bars 188, 190. After the guide body is secured, the surgeon mills a notch in the distal end of the femur by using the milling device of FIGS. 18–20 in a similar manner as described earlier. The bobbin shaped nose portion 158 of milling device 150 is accommodated by slot 196 to guide burr 168 in an anterior-posterior direction. With burr 168 rotating, a slot (not shown) is formed in the distal end of the resected femur.

Finally, with the notch milling guide 180 still attached, as described above, the surgeon resects the posterior condyles 3 with the use of a known oscillating saw and blade (not shown). The blade is accommodated within an aligned pair of laterally aligned slots 198. As illustrated, multiple pairs of laterally aligned slots 198 are provided to allow the surgeon to choose how much of the posterior condyles should be removed.

Once the posterior condyles have been removed, the milling of the distal femur is now complete and the femoral bases 50 may be removed by removing tapered bone screws 70. Typically, the surgeon at this point will use a provisional implant to check the fit of the milled bone with the implant and the knee joint is evaluated for a proper anatomical set up as determined by the surgeon. The surgeon may determine that in order to receive an optimum result, additional bone should milled from the femur. Such remilling requires the milling instruments to be aligned relative to the existing milled surfaces.

Figure 30:
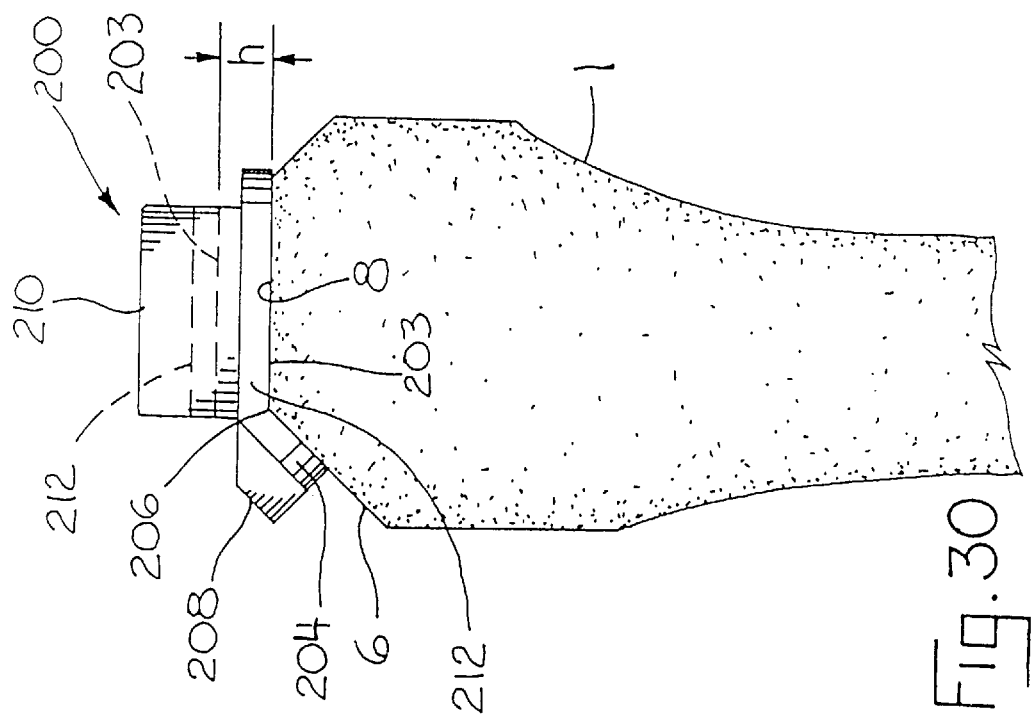
FIG. 30 is a side elevational view of the guide of FIG. 29 in contact with the resected distal femur.
Figure 29:
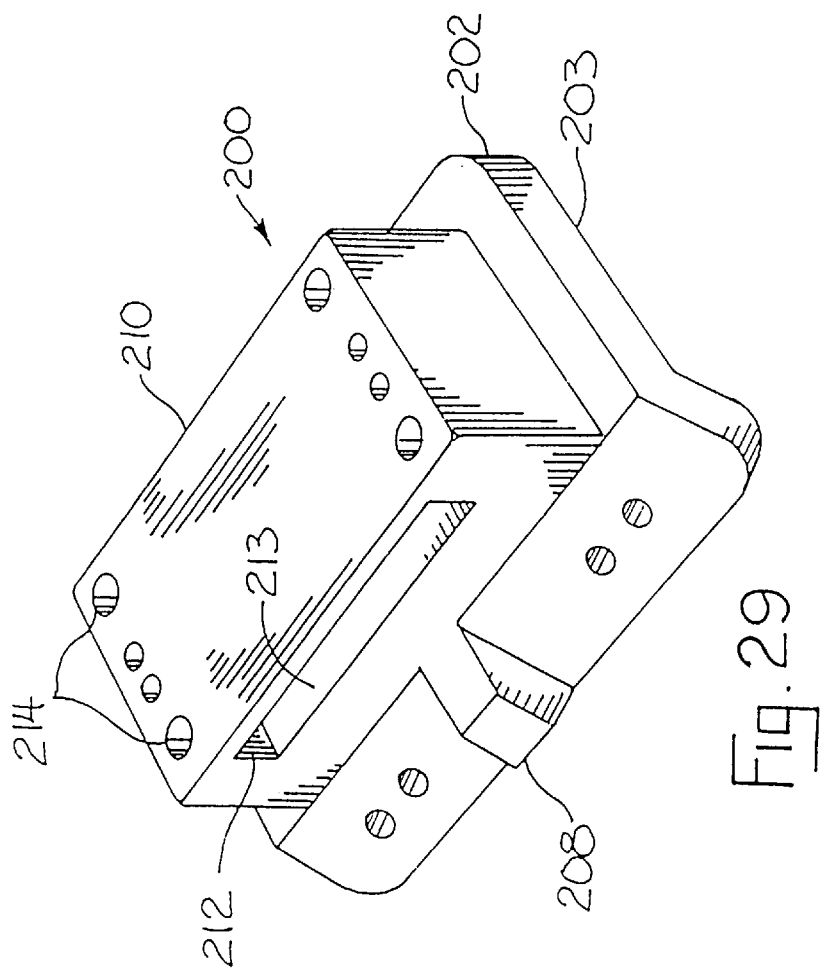
FIG. 29 is a perspective view of a remilling guide.
Figure 31:
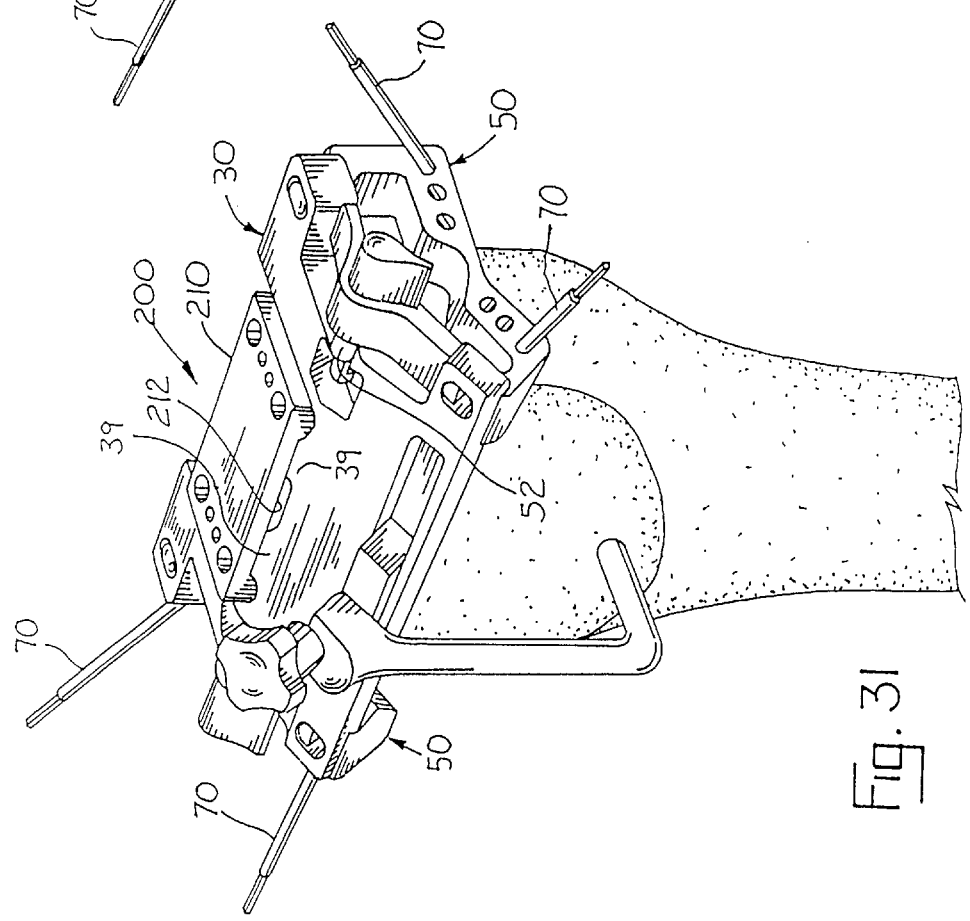
FIG. 31 is a perspective view of the remilling guide in use with the AP placement guide and femoral bases.
Figure 34:
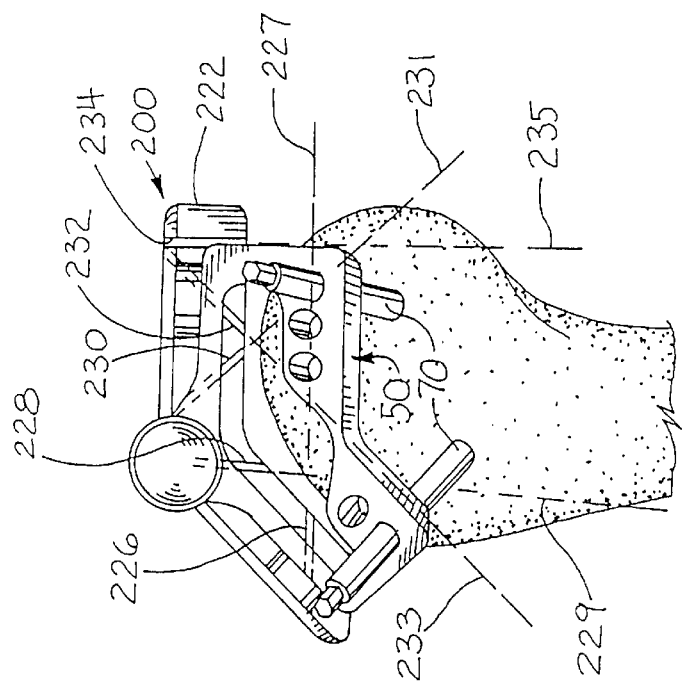
FIG. 34 is a side elevational view of FIG. 32.
Figure 33:
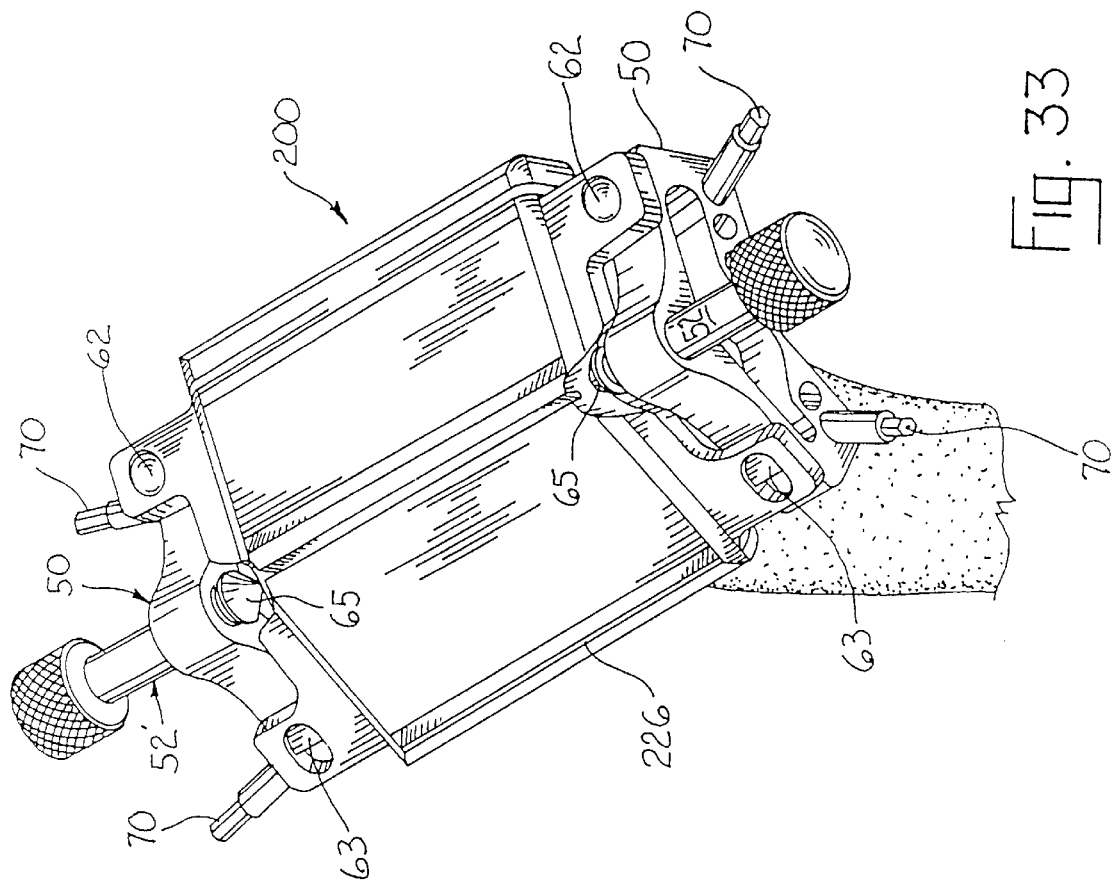
FIG. 33 is a perspective view of a one piece cutting guide connected to the femoral bases of the invention.

If remilling is required by the surgeon, the remilling alignment guide 200 of FIGS. 29–31 is implemented in the following manner to reattach the femoral bases 50 in alignment with the femur relative to the previously milled surfaces 6 and 8. As illustrated best in FIGS. 29 and 30, remilling alignment guide 200 includes a base 202 having an inclined anterior wall 204 which forms an obtuse corner 206 at its junction with base 202. As illustrated, corner 206 closely matches the angle formed by anterior chamfer surface 6 and distal surface 8 formed by the initially milling procedures as described above. This provides a precise alignment between the femur and the alignment guide 200. A projection 208 extends from inclined anterior wall 204 as illustrated. A housing 210 extends integrally from base 202 and includes a rectangular slot 212 and a plurality of through bores 214 as illustrated best in FIG. 29. Through bores 214 extend through base 202 and are provided to accommodate fastening devices such as screws or pins (not shown). The distance between wall 213 of slot 212 and the bone contacting surface 203 of base 202 is a predetermined distance "h" (see FIG. 20) and defines the amount of additional bone stock to be removed during the remilling procedure. As will be seen by decreasing the distance h, for example, by making base 202 thinner, the amount of bone to be removed is increased. Conversely, by increasing the thickness of the base 202 and thereby distance h, the amount of bone stock to be removed will be reduced. Alignment guide 200 is centered on the femur so that an equal amount to the femur is visible on the medial and lateral sides of the guide. Guide 200 may be secured in place by two or more pins or screws (not shown) accommodated by through bores 214.

Figure 32:
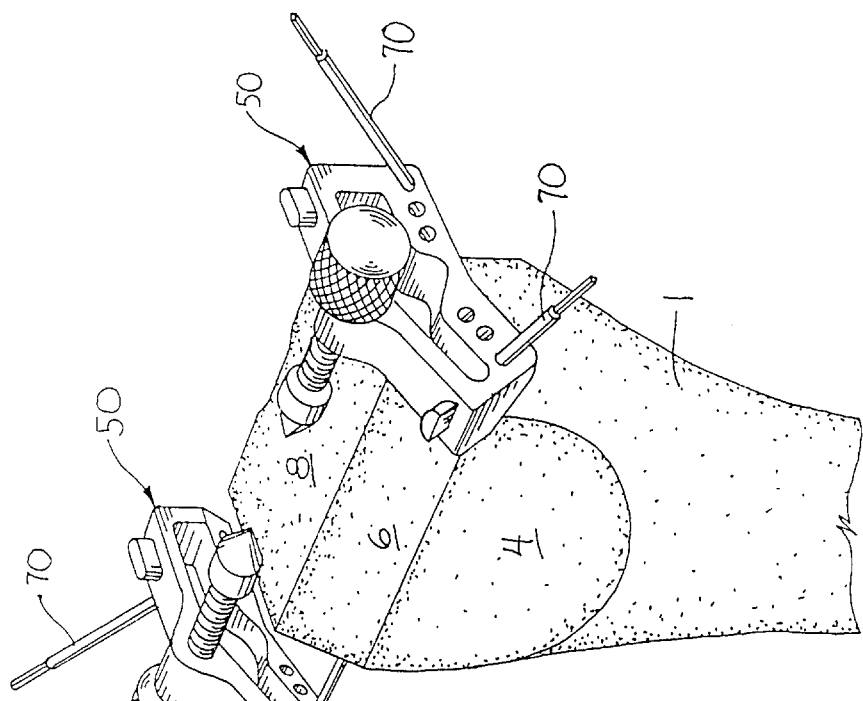
FIG. 32 is a perspective view of the femoral bases connected to the resected femur after alignment by the remilling guide as in FIG. 31.

After the remilling guide is aligned and attached to the femur as described above, the femoral bases 50 as used and described in detail earlier are reconnected to the AP alignment guide 30 which has also been described in detail previously in the specification. AP alignment guide 30 is slid on to remilling guide 200 with fingers 39 accommodated within the rectangular slot 212 of the remilling guide. With the AP alignment guide fully seated on the remilling guide (as illustrated in FIG. 31), the surgeon inserts a plurality tapered bone screw 70 to secure femoral bases 50 to the femur in the manner described previously. Once the bases are secure, the locking mechanisms 52 are disengaged to release the AP alignment guide and remilling guide which are then removed leaving only femoral bases 50 connected to the milled femur as illustrated in FIG. 32. From this point on, remilling of the femur is accomplished in exactly the same manner as described earlier using femoral milling guide 80 and notch milling guide 180 previously described. Since the reference points for these milling guides are bases 50, which were reconnected with reference to the milled surfaces by remilling guide 200, the amount of bone removed during remilling is determined by the remilling guide as mentioned earlier.

As an alternative to milling the bone using the various milling guides described above, the instrument set of this invention provides the surgeon the option of connecting a cutting guide to the femoral bases to resect the bone using a standard cutting device such as an oscillating powered surgical saw (not shown). The five in one cutting guide 220 of the instrument set of the invention is illustrated in FIGS. 33 through 37 and includes a body 222 including a slight bend therein as shown. A pair of tabs 224 extend from the medial and lateral edges of body 222 and include openings therein for accommodating the protrusions 62, 63 from femoral bases 50. A recess is formed in the medial and lateral sides of the body 22 for accommodating the conical tip 65 of the alternative locking mechanism 52' for base 50. A slot 226 is formed in body 222 inclined so as to guide a saw blade along the path illustrated by broken line 227 for resection of the distal surface of the femur. Slot 228 is formed in body 222 inclined so as to guide a saw blade along the path illustrated by broken line 229 for resection of the anterior condyle. A slot 230 is formed in body 222 inclined so as to guide a saw blade along the path illustrated by broken line 231 for forming a posterior chamfered surface. A slot 232 is formed in body 222 inclined so as to guide a saw blade along the path illustrated by broken line 233 for forming an anterior chamfered surface. Finally, a pair of aligned slots 234 are provided in base 222 for guiding a saw blade along the path illustrated by broken line 235 for the resection of the posterior condyles. In use, the surgeon establishes the femoral bases 50 in the same manner as described above with reference to the milling guides of the invention. However, instead of connecting the femoral milling guide 80 to the bases, the surgeon attaches the five in one cutting guide 220 to the bases. With the cutting guide connected to the bases, the surgeon inserts a blade through each slot to make all the cuts necessary for placement of a prosthetic knee without ever moving, shifting or otherwise reorienting or changing the five in one cutting guide. By making all the cuts necessary without changing guides, the relative precision between the cuts made can be more precisely controlled thus leading to a better fitting implant.

Once the surgeon has resected the femur using the five in one cutting guide, it is typical that a provisional implant will be used to determine fit of the total implant. If the surgeon determines that additional bone should be removed to optimize the fit of the implant, the remilling guide 200 and AP alignment guide 30 is used to reestablish the femoral bases 50 in the same manner as described above. The cutting guide 220 is then reattached to the bases and the femur is re-cut.

It should be understood that the invention is not to be limited to the precise details above but may be modified within the scope of the appended claims.

We claim:

1. A milling device and guide for milling portions of the end of an exposed bone, said milling device for being accommodated by said guide, said guide a guide having at least one slot defined by substantially parallel sides having a predetermined thickness between said sides, said milling device having a housing terminating in an end, a plate being spaced from said end and connected thereto by a tubular shaft such that said end is spaced from said plate by said tubular shaft a distance slightly greater than said predetermined thickness, the milling device also includes a burr shaft extending into the tubular shaft and a burr carried by said burr shaft is adjacent the plate, a motor means connected to an energy source and to said burr shaft to rotate the burr shaft and burr.

2. The milling device of claim 1 including a sleeve carried by the milling device and being shiftable between an extended position about said end and a retracted position spaced from the end such that said end and the burr are exposed.

3. The milling device of claim 2 wherein the sleeve cooperates with a milling guide to align the burr with the milling guide.

* * * * *